United States Patent [19]

Tam et al.

[11] Patent Number: 4,832,914
[45] Date of Patent: May 23, 1989

[54] TWO-DIMENSIONAL UNIFORMLY FED UNSTIRRED CHEMICAL REACTOR

[75] Inventors: Wing Y. Tam; Werner Horsthemke; William D. McCormick; Harry L. Swinney, all of Austin, Tex.

[73] Assignee: Board of Regents/The University of Texas System, Austin, Tex.

[21] Appl. No.: 153,638

[22] Filed: Feb. 8, 1988

[51] Int. Cl.[4] ..................... G01N 21/75; G01N 33/559
[52] U.S. Cl. ....................... 422/130; 422/55; 422/58; 422/99; 436/515; 73/864.72
[58] Field of Search ............... 422/130, 78, 86, 87, 422/99, 58; 436/165, 170, 515; 73/864.72

[56] References Cited

U.S. PATENT DOCUMENTS 3,554,704  2/1969  Ushakoff .................. 436/515 X
3,718,436  2/1973  Ushakoff .................. 422/58
3,960,489  6/1976  Giaever ................... 422/55 X
4,731,335  3/1988  Brigati ................... 73/864.72

FOREIGN PATENT DOCUMENTS 2424426  6/1975  Fed. Rep. of Germany ... 73/864.72

Primary Examiner—Benoit Castel
Assistant Examiner—Amalia L. Santiago
Attorney, Agent, or Firm—Michael F. Esposito; Joseph G. Curatolo; Larry W. Evans

[57] ABSTRACT

An apparatus and method for producing and observing spatial patterns in chemical reaction comprising a vessel having a laminate positioned in said vessel forming a chamber. The laminate comprises a polymer gel layer (or other porous medium) sandwiched between a transparent layer and an array of capillary tubes. The capillaries in the array are perpendicular to the gel surface in order to allow access to the gel from the chamber only in a direction perpendicular to the surface of the gel.

4 Claims, 1 Drawing Sheet

TWO-DIMENSIONAL UNIFORMLY FED UNSTIRRED CHEMICAL REACTOR

BACKGROUND OF THE INVENTION

The present invention is directed to a process for generating spatiotemporal patterns in a chemical reaction and the device for producing the patterns. In particular, the present invention is directed to a process and device for the creation of spatiotemporal patterns by the uniform feeding of the materials into a reactor in a manner so that convective motion does not interfere with the chemical pattern achieved during the reaction. The process and reactor of the present invention has specific utility in the study of various spatial patterns of chemical reactions to understand the particular mechanism of the reaction and also as a means for concentrating highly desirable chemical intermediates in a specific area of the solution so that these highly desirable chemical materials may be extracted in greater concentrations. Specifically, the process and apparatus may be utilized in biological methods wherein small amounts of highly valuable enzymes are produced and are difficult to separate because of their low concentration.

In the discussion of the process and apparatus of the present invention, specific reference will be made to the Belousov-Zhabotinsky (BZ) reaction system which has been studied for a number of years in an attempt to understand the formation of chemical spatial structures (mainly chemical waves) formed in a chemical reaction. For a detailed description of that work see Vidal et al., "Etude . . . Oscillant", J. *Physique,* 47, pp. 1999-2009, November 1986, herein incorporated by reference.

Many experiments on spatial self organization in chemical systems have yielded spiral waves and concentric ring patterns. Those experiments were conducted in closed reactors. Hence, the systems evolved irreversibly and uncontrollably toward thermodynamic equilibrium. The transient nature of the spatial patterns and the lack of a well-defined control parameter complicates the interpretation of these experiments and existing theories concerning the asymptotic (long time) states. About a decade ago, the CSTR (continuous flow stirred tank reactor) replaced closed reactors in experiments on well mixed oscillating chemical reactions. Subsequently a wide variety of new dynamical phenomena were discovered in the study of these oscillating chemical reactions.

The present invention is directed to a continuously fed unstirred reactor which can serve as a tool for the systematic study of the spatial patterns generated in these oscillating chemical reactions. The continuously fed unstirred reactor of the present invention (CFUR) can be maintained indefinitely at a fixed distance away from equilibrium by the continuous feed of the chemical reagents. The advantage of the CFUR of the present invention is that a porous medium, in the present embodiment a polymeric gel, prevents the occurrence of convective motion in the reaction. Convective motion has plagued previous studies of pattern formation in chemical reactions. A second advantage of the CFUR of the present invention is the use of a capillary array plate to achieve a uniform feed of the gel layer and a decoupling from the turbulent flow in the mixing chamber.

SUMMARY OF THE INVENTION

It is the primary object of the present invention to provide a novel chemical reactor used to generate and maintain spatial patterns in an on-going chemical reaction.

It is a second object of the present invention to provide a process for the generation and maintenance of spatiotemporal patterns in an on-going chemical reaction.

Additional objects and advantages of the invention will be set forth in part in the description which follows and in part will be obvious in the description or may be learned by the practice of the invention. The objects and advantages of the invention may be realized and attained by means of the instrumentalities and combinations particularly pointed out in the appended claims.

To achieve the foregoing objects and in accordance with the purpose of the present invention as embodied and broadly described herein, the reactor of the present invention comprises a vessel having a laminate positioned in said vessel forming a chamber the laminate comprising an inert porous medium sandwiched between a clear transparent layer and a capillary array plate, the capillary array plate being positioned between the porous medium and the chamber in order to allow access between the chamber and the porous medium through capillaries perpendicular to the pourous medium.

In particular, the reactor of the present invention is composed of three parts: a continuously stirred reactor that serves as a mixing chamber, a capillary array plate and a diffusion reactor. The mixing chamber is a chamber with input lines for the various feed chemicals and an output line. One wall of the chamber is formed by the capillary array plate. The capillary array plate is a thin plate formed by an array of glass capillary tubes having their axes perpendicular to the plane of the plate. The capillaries are open on both ends permitting the chemicals in the stirred reactor to come into contact diffusively with the diffusion reactor. The diffusion reactor is a thin layer of an inert porous material, in the present embodiment a polymeric gel, in contact with the capillary array plate on one side and an impervious but optically transparent plate on the other side. This transparent plate serves as one wall of the reactor, and also as a window through which the diffusion reactor may be observed. The diffusion reactor is the part of this system in which spatial patterns are generated and maintained.

In a further embodiment of the present invention the process of producing spatial patterns in a chemical reaction comprises introducing the chemical ingredients to be reacted into a vessel having a chamber and a laimnate positioned adjacent to the chamber in direct contact with the chamber, the laimnate comprising an inert porous medium sandwiched between a transparent layer and a capillary array plate, the capillaries in said array plate being arranged perpendicular to the porous medium and the chamber to allow access to the porous medium from the chamber, reacting the ingredients in the chamber and transporting the reacting solution from the chamber into the porous medium via the capillary array resulting in the generation of a spatial pattern in the porous medium.

In particular, the process of maintaining spatiotemporal patterns is achieved in the following way: Appropriate chemicals are fed continuously into the mixing chamber and come into contact with the capillary array plate. The mixture diffuses through the capillary array plate and into the diffusion reactor where spatial or spatiotemporal structures may be formed. The porous material in the reactor serves as an inert medium in which chemical reaction and diffusion can take place, allowing the formation of the aforementioned structures, but preventing either convection or the formation of bubbles which could destroy the structures. No spatial structures can be formed in the capillary array plate itself since the capillaries do not permit lateral diffusion. The capillary array plate thus serves to allow diffusive exchange between the mixing chamber and the diffusion reactor while preventing the turbulent fluid motions in the former from affecting spatial structures in the latter.

The major advantages of the process and apparatus of the present invention are:

(1) The capillary array plate between the thin gel layer and the mixing chamber prevents lateral diffusion in the chemical feed in the region adjacent to the gel; without the capillary array plate patterns could form as a consequence of lateral diffusion in the feed and these patterns would interfere with patterns formed in the gel. The capillary array plate also separates the stirred reservoir from the region in which patterns form (the gel); thus, the capillary array plate prevents the stirring of the reservoir from disturbing pattern formation in the gel.

(2) The use of a gel or other inert medium prevents mass motion or convection that would interfere with the formation of a chemical reaction-diffusion pattern. In the absence of the gel, mass motion or convection could break up or modify the chemical patterns. Thus, the pattern in the gel arises solely from reaction-diffusion effects and not from hydrodynamic effects or from a combination of hydrodynamic and reaction-diffusion effects.

The accompanying drawing which is incorporated and constitutes a part of this specification illustrates a preferred embodiment of the invention and together with the description, serves to explain the principles of the invention.

DETAILED DESCRIPTION OF THE INVENTION

Figure 1:
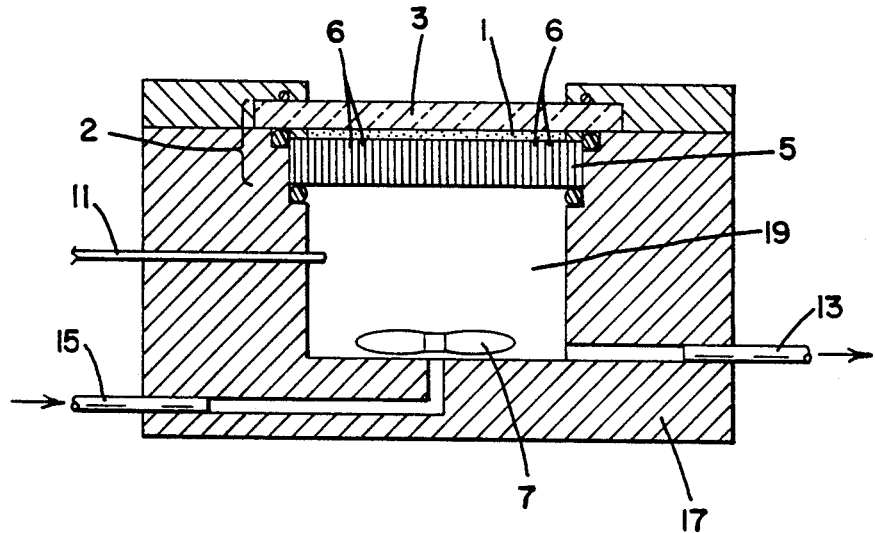
FIG. 1 is a cross-sectional view of the continuously fed unstirred reactor system of the present invention.

Reference will now be made in detail to the present preferred embodiment of the invention which is illustrated by the accompanying drawing.

FIG. 1 is a cross-sectional view of the apparatus of the present invention. Vessel 17 contains a mixing chamber 19 having a magnetic stirrer 7. The outer walls of vessel 17 contain inlet 15 and outlet 13. Electrode 11 is positioned through an outside wall of vessel 17 into chamber 19. Laminate 2 comprises a sandwiched structure having polymer gel 1 sandwiched between a transparent plate 3 and a capillary array plate 5. Capillary array plate 5 is between chamber 19 and gel 1 with the capillary tubes 6 arranged perpendicular to the gel 1. Transparent plate 3 may be made of any transparent material such as glass provided that it does not interfere with the ongoing chemical reaction occurring in the polymer gel. The polymer gel material must be inert to the chemical materials that are reacting. In the case of the BZ reaction which involves the use of $H_2SO_4$, $KBrO_3$, malonic acid and ferro ion ($Fe+2$) catalyst in an aqueous solution, a suitable polymeric material is polyacrylamide.

In operation, chemical ingredients are passed through inlet 75 into chamber 19 where they are mixed utilizing magnetic stirrer 7. The reacting solution in chamber 19 is then diffused through the capillary array plate 5 into gel 1 where the chemical reaction continues. The reaction in gel 1 is observed through transparent plate 3 and the spatial waves being generated during the chemical reaction can be studied. The capillary array plate is arranged so that diffusion into the gel layer only takes place normal to the surface of the gel. The gel prevents convective motion and inhibits any bubble formation. This prevents the destruction of the desired spatiotemporal chemical pattern formation taking place in the gel. The array plate ensures that only mass transport normal to the gel occurs and that no undesirable chemical coupling between the patterns in the gel layer and the turbulence of the chemical solution in chamber 19 breaks up the pattern in the gel layer. This leads to a clear undisturbed observation of the spatiotemporal waves created during the chemical reaction. The concentration of highly desirable chemical intermediates at certain positions in spatiotemporal pattern is orders of magnitude higher than the background concentrations. Therefore, extraction at these points of the spatiotemporal pattern allows one to extract highly desirable chemical intermediates or biological enzymes in higher concentrations than previously achieved.

Electrode 11 is placed through vessel 17 into chamber 19 to monitor the concentration of the chemical or biological solution in the chamber. Outlet 13 through chamber 19 is to ensure that the reaction volume of the solution in chamber 19 can be maintained relatively constant. It is, of course, understood that the laminate placed in vessel 17 should be sealed to prevent leakage of the chemical solution from chamber 19 into gel 1. This may be done by utilizing any conventional sealing material inert to the chemical being utilized and its selection does not form a part of the present invention.

The foregoing description of the preferred embodiment of the invention has been presented for purposes of illustration and description. It is not intended to be exhaustive or to limit the invention to the precise form disclosed, and obviously many modifications and variatios are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for use in producing and observing spatiotemporal patterns in chemical reactions comprising a vessel having a laimnate positioned in said vessel forming a chamber, said laminate comprising an inert porous medium, a clear transparent layer and a capillary array plate, wherein said inert porous medium is sandwiched between said clear transparent layer and said capillary array plate, the capillaries in said capillary array plate being positioned perpendicular to said inert porous medium and said chamber in order to allow access to said porous medium from said chamber.

2. The apparatus of claim 1 wherein the inert porous medium is a polymer gel.

3. A process for the production of spatial patterns in a chemical reaction comprising introducing chemical reactants into a vessel having a chamber formed by a laminate positioned adjacent to said vessel in direct contact with said vessel, the laminate comprising an inert porous medium, a clear transparent layer and a capillary array plate, wherein said inert porous medium is sandwiched between said transparent layer and said capillary array plate, the capillaries in said array plate being arranged perpendicular to said porous medium and said chamber to allow access to said porous medium from said chamber, thereby reacting said chemicals in said chamber and transporting the reacting solution from said chamber to said porous medium via said capillaries to continue said reaction in said porous medium thereby resulting in the generation of a spatial pattern in said porous medium.

4. The process of claim 3 wherein the inert porous medium is a polymer gel.

* * * * *